(12) United States Patent
Kataoka et al.

(10) Patent No.: US 7,687,056 B2
(45) Date of Patent: Mar. 30, 2010

(54) THERAPEUTIC AGENTS FOR RENAL DISEASES

(75) Inventors: Motoyuki Kataoka, Kamakura (JP); Keigo Yorozu, Kamakura (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/575,263

(22) PCT Filed: Oct. 14, 2004

(86) PCT No.: PCT/JP2004/015127

§ 371 (c)(1),
(2), (4) Date: Apr. 10, 2006

(87) PCT Pub. No.: WO2005/034986

PCT Pub. Date: Apr. 21, 2005

(65) Prior Publication Data

US 2007/0020231 A1    Jan. 25, 2007

(30) Foreign Application Priority Data

Oct. 14, 2003    (JP) .............................. 2003-353076

(51) Int. Cl.
*A61K 38/18*    (2006.01)
*A61P 13/12*    (2006.01)
(52) U.S. Cl. ..................................... 424/85.1; 530/351
(58) Field of Classification Search ........................ None
See application file for complete search history.

(56) References Cited

U.S. PATENT DOCUMENTS

| 5,496,804 | A | | 3/1996 | Reed et al. |
| 5,679,356 | A | * | 10/1997 | Bonnem et al. .......... 424/278.1 |
| 5,855,913 | A | * | 1/1999 | Hanes et al. ................. 424/489 |
| 6,355,239 | B1 | * | 3/2002 | Bruder et al. ............... 424/93.1 |
| 6,689,351 | B1 | * | 2/2004 | Pierce et al. ................ 424/85.1 |
| 2004/0019184 | A1 | * | 1/2004 | Fukuda et al. .............. 530/350 |

OTHER PUBLICATIONS

Nicholls AJ., The impact of atherosclerotic renovascular disease on diabetic renal failure. Diabetic Medicine, 19, 889-894, 2002.*
Florian Togel et al., "Hematopoietic Stem Cell Mobilization-Associated Granulocytosis Severely Worsens Acute Renal Failure", *J. Am. Soc. Nephrol*, vol. 15, pp. 1261-1267, 2004.
Kanji Shishido et al., "The effects and pharmacokinetics of rhG-CSF on the treatment of neutropenia in patients with renal failure", *Jpn. J. Nephrol*, vol. 33, No. 10, pp. 973-981, Aug. 31, 1991.
Akiko Saeki et al., "Impaired neutrophil function in chronic renal failure-Disregulation of surface adhesion molecule expression and phagocytosis", *Jpn. J. Nephrol. Society*, vol. 38, No. 12, pp. 585-594, Sep. 17, 1996.
F. Strutz et al., "On the Progression of Chronic Renal Disease", *Nephron*, vol. 69, pp. 371-379, 1995.

* cited by examiner

*Primary Examiner*—Lorraine Spector
*Assistant Examiner*—Elly-Gerald Stoica
(74) *Attorney, Agent, or Firm*—Browdy and Neimark, PLLC

(57) ABSTRACT

The present invention relates to therapeutic agents for renal diseases containing a colony-stimulating factor (CSF) as an active ingredient and renal tissue repairing/regenerating agents containing a colony-stimulating factor (CSF) as an active ingredient. The colony-stimulating factor (CSF) is preferably granulocyte colony-stimulating factor (G-CSF).

5 Claims, No Drawings

THERAPEUTIC AGENTS FOR RENAL DISEASES

TECHNICAL FIELD

The present invention relates to novel therapeutic agents for renal diseases and renal tissue repairing/regenerating agents. The therapeutic agents for renal diseases and renal tissue repairing/regenerating agents of the present invention contain a colony-stimulating factor (CSF) as an active ingredient.

BACKGROUND ART

Human G-CSF is a hematopoietic factor discovered as a differentiation-inducing factor of granulocyte lineage hematopoietic stem cells, and clinically used as a therapeutic agent for neutropenia after bone marrow transplantation or chemotherapy for cancer because it stimulates production of neutrophil in vivo. In addition to the function above, human G-CSF also acts on stem cells to stimulate their differentiation and proliferation, or mobilizes stem cells from the bone marrow into the peripheral blood. Peripheral blood stem cell transplantation has been actually performed in the clinical field on the basis of the latter function by transplanting peripheral blood hematopoietic stem cells mobilized by human G-CSF for the purpose of stimulating the recovery of hematopoiesis in cancer patients after high doze chemotherapy. However, there has been no report that G-CSF is used for renal diseases therapy.

DISCLOSURE OF THE INVENTION

Problems to be Solved by the Invention

An object of the present invention is to provide a method for treating renal diseases and a method for repairing or regenerating kidneys.

Problems to be Solved by the Invention

We studied effects of G-CSF in treating renal diseases and repairing/regenerating kidneys. As a result, we found that damaged renal tissue is repaired by administration of G-CSF and therefore, G-CSF is useful as a therapeutic agent for renal diseases and as a renal tissue repairing/regenerating agent. The present invention was accomplished on the basis of this finding.

Accordingly, the present invention provides the following.

(1) A therapeutic agent for a renal disease containing a colony-stimulating factor (CSF) as an active ingredient.

(2) The therapeutic agent as defined in (1) above wherein the colony-stimulating factor is granulocyte colony-stimulating factor (G-CSF).

(3) The therapeutic agent as defined in (1) or (2) above wherein the renal disease is chronic renal failure.

(4) The therapeutic agent as defined in (1) or (2) above wherein the renal disease is acute renal failure.

(5) The therapeutic agent as defined in (1) or (2) above wherein the renal disease is nephropathy.

(6) The therapeutic agent as defined in (5) above wherein the renal disease is diabetic nephropathy.

(7) The therapeutic agent as defined in (5) above wherein the renal disease is atherosclerotic nephropathy.

(8) A renal tissue repairing/regenerating agent containing a colony-stimulating factor (CSF) as an active ingredient.

(9) The repairing/regenerating agent as defined in (8) above wherein the colony-stimulating factor is granulocyte colony-stimulating factor (G-CSF).

(10) A method for proliferating or regenerating renal tissue or a cell present in renal tissue by contacting G-CSF with the renal tissue or the cell present in renal tissue.

THE MOST PREFERRED EMBODIMENTS OF THE INVENTION

The therapeutic agents for renal diseases of the present invention contain a colony-stimulating factor (CSF) as an active ingredient. The CSF may be granulocyte colony-stimulating factor (G-CSF), macrophage colony-stimulating factor (M-CSF), granulocyte-macrophage colony-stimulating factor (GM-CSF), etc., but G-CSF is preferably used in the present invention.

The renal disease targeted by the therapeutic agents of the present invention is not specifically limited and may be any renal disease such as renal failure, nephropathy, obstructive nephropathy, etc., but preferably renal failure or nephropathy.

Renal failure generally means a condition in which nitrogen metabolism and excretion; water, electrolyte and acid-base balance; as well as the production, secretion and metabolism of physiologically active materials such as kidney-specific hormones are inhibited by a loss of renal function ("New Clinical Internal Medicine", published by Igaku-Shoin, 2002, 1289-1296, 1331-1335).

Renal failure is classified into chronic renal failure (CRF) and acute renal failure (ARF), and either chronic renal failure or acute renal failure may be targeted by the therapeutic agents of the present invention. Acute renal failure is subclassified into prerenal acute renal failure caused by decreased blood flow; postrenal acute renal failure caused by bilateral urinary tract obstruction; intrinsic acute renal failure caused by renal parenchymal injury, etc. Causes of chronic renal failure include diabetic nephropathy, chronic glomerular nephritis, nephrosclerosis, polycystic kidney disease, etc.

The nephropathy targeted by the therapeutic agents of the present invention is not specifically limited and may be any nephropathy such as systemic disease-induced nephropathy, drug-induced nephropathy, heavy metal-induced nephropathy, etc. Systemic disease-induced nephropathy may be nephropathy induced by diabetes, arteriosclerosis, systemic lupus erythematosus, progressive systemic sclerosis, rheumatoid arthritis, mixed connective tissue disease, cryoglobulinemia, polyarteritis nodosa, Wegener's granulomatosis, Schonlein-Henoch purpula, etc., but preferably diabetic nephropathy or arteriosclerotic nephropathy. Drug-induced nephropathy may be nephropathy induced by anticancer agents, antibiotics (e.g., penicillin, cephem, aminoglycoside, polypeptide or antifungal antibiotics), analgesics (non-steroid anti-inflammatory drugs), immunosuppressants (e.g., cyclosporin A), contrasts, penicillamine, lithium, heroin, tolbutamide, probenecide, cimetidine, etc. Heavy metal-induced nephropathy may be nephropathy induced by mercury, lead, platinum, gold, silver, copper, cadmium, iron, etc.

The therapeutic agents of the present invention can also be used as renal repairing/regenerating agents. Thus, the present invention relates to renal repairing/regenerating agents containing a colony-stimulating factor, especially G-CSF as an active ingredient.

A kidney to be repaired/regenerated in the present invention may be any kidney such as injured kidney, necrotic kidney, resected kidney, etc. For example, the repairing/regenerating agents of the present invention can be used when renal tissue must be repaired or regenerated in e.g., a kidney injured by a drug or the like or a kidney necrosed by insufficient blood flow.

The kidney can be repaired/regenerated by administering a repairing/regenerating agent of the present invention in vivo or adding a repairing/regenerating agent of the present invention to renal tissue cultures in vitro.

Decreased or lost renal function can be recovered by the renal tissue repairing/regenerating agents of the present invention. Evaluation of renal function is generally known and can be performed by a method known to those skilled in the art. For example, the evaluation can be performed on the basis of the BUN (blood urea nitrogen) level, creatinine level, etc.

The present invention also relates to methods for proliferating or regenerating renal tissue or a cell present in renal tissue by contacting G-CSF with the renal tissue or the cell present in renal tissue. G-CSF can be contacted with the renal tissue or the cell present in renal tissue in vivo or in vitro.

Renal tissue consists of renal parenchyma (glomerulus, proximal tubule, Henle's loop, distal tubule, collecting duct, Bowman's capsule, efferent arteriole, etc.), renal pelvis and the like, and cells present in renal tissue include mesangial cells, endothelial cells, epithelial cells, renin secreting cells, collecting duct principal cells (P cells), collecting duct intercalated cells (I cells), etc.

The G-CSF used as an active ingredient of the therapeutic agents for renal diseases or renal repairing/regenerating agents of the present invention can be any G-CSF, but preferably highly purified G-CSF, more specifically mammalian G-CSF, especially that having biological activity substantially identical to that of human G-CSF. The source from which the G-CSF is derived is not specifically limited, and naturally derived G-CSF or genetically engineered G-CSF can be used, preferably genetically engineered G-CSF. Genetically engineered G-CSF may have an amino acid sequence identical to that of naturally derived G-CSF, or may contain a deletion, substitution, addition or other modification of one or more amino acids in such amino acid sequence, so long as it has similar biological activity to that of naturally derived G-CSF. Deletion, substitution, addition or other modification of amino acids can be performed by a method known to those skilled in the art. For example, a polypeptide functionally comparable to G-CSF can be prepared by those skilled in the art by introducing an amino acid variation into G-CSF as appropriate using site-directed mutagenesis (Gotoh, T. et al. (1995) Gene 152, 271-275; Zoller, M. J. and Smith, M. (1983) Methods Enzymol. 100, 468-500; Kramer, W. et al. (1984) Nucleic Acids Res. 12, 9441-9456; Kramer, W. and Fritz, H. J. (1987) Methods Enzymol. 154, 350-367; Kunkel, T. A. (1985) Proc. Natl. Acad. Sci. USA. 82, 488-492; Kunkel (1988) Methods Enzymol. 85, 2763-2766) or other techniques. Amino acid variations also occur in nature. Generally, an amino acid residue is preferably substituted by another amino acid in which the property of the amino acid side chain is conserved. For example, the properties of amino acid side chains include hydrophobic amino acids (A, I, L, M, F, P, W, Y, V), hydrophilic amino acids (R, D, N, C, E, Q, G, H, K, S, T), amino acids having aliphatic side chains (G, A, V, L, I, P), amino acids having hydroxyl-containing side chains (S, T, Y), amino acids having sulfur-containing side chains (C, M), amino acids having carboxylate- and amide-containing side chains (D, N, E, Q), amino acids having base-containing side chains (R, K, H), and amino acids having aromatic-containing side chains (H, F, Y, W) (examples shown by one-letter amino acid codes within each set of parentheses). It is already known that polypeptides having an amino acid sequence modified by deleting, adding and/or substituting one or more amino acid residues retain their biological activity (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G. et al., Proc. Natl. Acad. Sci. USA (1982) 79, 6409-6413).

Fusion proteins of G-CSF and another protein can also be used. Fusion proteins can be prepared by e.g. ligating the DNA encoding G-CSF in-frame with the DNA encoding another protein, inserting the ligation product into an expression vector and expressing it in a host. The second protein to be fused to G-CSF herein is not specifically limited.

Chemically modified G-CSF can also be used. Examples of chemically modified G-CSF include, for example, G-CSF manipulated to have a conformational change or addition or deletion of oligosaccharide chains and G-CSF conjugated to polyethylene glycol, vitamin B12 or a compound such as an inorganic or organic compound.

The G-CSF used in the present invention can be prepared by any process, e.g. by culturing a human tumor cell or a cell line of a human G-CSF-producing hybridoma and extracting and isolating/purifying G-CSF by various methods from the cultured cell or by producing G-CSF by genetic engineering techniques in *E.coli*, yeast, Chinese Hamster Ovary cells (CHO cells), C127 cells, COS cells, myeloma cells, BHK cells, insect cells or the like and extracting and isolating/purifying it by various methods. The G-CSF used in the present invention is preferably G-CSF prepared by genetic engineering techniques, preferably using mammalian cells (especially CHO cells) (e.g., see JPB HEI 1-44200, JPB HEI 2-5395, JPA SHO 62-129298, JPA SHO 62-132899, JPA SHO 62-236488, and JPA SHO 64-85098).

The therapeutic agents for renal diseases or renal repairing/regenerating agents of the present invention can contain suspending agents, solubilizers, stabilizers, isotonizing agents, preservatives, adsorption inhibitors, surfactants, diluents, excipients, pH modifiers, soothing agents, buffers, sulfur-containing reducing agents, antioxidants, etc. as appropriate depending on the mode of administration or dosage form, if desired.

Examples of suspending agents include methylcellulose, Polysorbate 80, Polysorbate 20, hydroxyethylcellulose, gum acacia, gum tragacanth powder, sodium carboxymethylcellulose, polyoxyethylene sorbitan monolaurate, etc.

Solubilizers include polyoxyethylene hydrogenated castor oil, Polysorbate 80, Polysorbate 20, nicotinic acid amide, Macrogols, castor oil fatty acid ethyl esters, etc.

Stabilizers include dextran 40, methylcellulose, gelatin, sodium sulfite, sodium metasulfite, etc.

Isotonizing agents include e.g., D-mannitol, sorbitol, etc.

Preservatives include e.g., methyl paraoxybenzoate, ethyl paraoxybenzoate, sorbic acid, phenol, cresol, chlorocresol, etc.

Adsorption inhibitors include e.g., human serum albumin, lecithin, dextran, ethylene oxide/propylene oxide copolymers, hydroxypropylcellulose, methylcellulose, polyoxyethylene hydrogenated castor oil, polyethylene glycol, etc.

Typical examples of surfactants include:

nonionic surfactants, e.g., sorbitan fatty acid esters such as sorbitan monocaprylate, sorbitan monolaurate, sorbitan monopalmitate; glycerin fatty acid esters such as glycerin monocaprylate, glycerin monomyristate, glycerin monostearate; polyglycerin fatty acid esters such as decaglyceryl monostearate, decaglyceryl distearate, decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate; polyoxyethylene sorbitol fatty acid esters such as polyoxyethylene sorbitol tetrastearate, polyoxyethylene sorbitol tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol ether, polyoxyethylene polyoxypropylene propyl ether, polyoxyethylene polyoxypropylene cetyl ether; polyoxyethylene alkyl phenyl ethers such as polyoxyethylene nonyl phenyl ether; polyoxyethylene hardened castor oils such as polyoxyethylene castor oil, polyoxyethylene hardened castor oil (polyoxyethylene hydrogenated castor oil); polyoxyethylene beeswax derivatives such as polyoxyethylene sorbitol beeswax; polyoxyethylene lanolin derivatives such as polyoxyethylene lanolin; polyoxyethylene fatty acid amides such as polyoxyethylene stearic acid amide having an HLB of 6-18;

anionic surfactants, e.g., alkyl sulfates having a C10-18 alkyl group such as sodium cetyl sulfate, sodium lauryl sulfate, sodium oleyl sulfate; polyoxyethylene alkyl ether sulfates having an average ethylene oxiside mole number of 2-4 and a C10-18 alkyl group such as sodium polyoxyethylene lauryl sulfate; alkyl sulfosuccinic acid ester salts having a C8-18 alkyl group such as sodium laurylsulfosuccinate; and natural surfactants, e.g., lecithin; glycerophospholipids; sphingophospholipids such as sphingomyelin; sucrose fatty acid esters of C12-18 fatty acids. Formulations of the present invention can contain one of these surfactants or more than one in combination. Preferred surfactants are polyoxyethylene sorbitan fatty acid esters such as Polysorbate 20, 40, 60 or 80, especially Polysorbates 20 and 80. Polyoxyethylene polyoxypropylene glycols such as poloxamers (e.g. Pluronic F-68®) are also preferred.

Sulfur-containing reducing agents include e.g., N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and sulfhydryl-containing compounds such as thioalkanoic acid having 1 to 7 carbon atoms.

Antioxidants include e.g., erythorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium bisulfite, sodium sulfite, triamyl gallate, propyl gallate or chelating agents such as disodium ethylenediamine tetraacetate (EDTA), sodium pyrophosphate and sodium metaphosphate.

Other components commonly added may also be contained, e.g., inorganic salts such as sodium chloride, potassium chloride, calcium chloride, sodium phosphate, potassium phosphate and sodium bicarbonate; and organic salts such as sodium citrate, potassium citrate and sodium acetate.

The therapeutic agents for renal diseases or renal repairing/regenerating agents of the present invention can be administered as injectables (e.g., for subcutaneous, intradermal, intramuscular, intravenous, intraperitoneal or intrarenal administration) or as dosage forms suitable for percutaneous, mucosal, nasal or the like administration or as dosage forms suitable for oral administration (tablets, capsules, granules, solutions, suspensions, etc.). The present invention is not limited by any administration route or dosage form.

Injectables are prepared by dissolving the components described above in an aqueous buffer known in the field of solution formulations such as a phosphate buffer (preferably sodium monohydrogen phosphate-sodium dihydrogen phosphate system) and/or a citrate buffer (preferably sodium citrate buffer) and/or an acetate buffer to prepare a solution formulation. The concentration of the buffer is normally 1-500 mM, preferably 5-100 mM, more preferably 10-20 mM. Injectables may be solution formulations or freeze-dried formulations.

The dose and frequency of the therapeutic agents for renal diseases or renal repairing/regenerating agents containing G-CSF as an active ingredient of the present invention can be determined as appropriate by those skilled in the art with consideration given to the condition of the patient having the target disease, but normally G-CSF can be administered at a dose of 0.1 to 500 µg/kg/day, preferably 0.5 to 20 µg/kg/day per adult. The frequency can be 1 to 7 days per week. However, the present invention is not limited by the dose of human G-CSF.

The therapeutic agents for renal diseases or renal repairing/regenerating agents of the present invention may be used in combination with other drugs.

Effects of the therapeutic agents for renal diseases or renal repairing/regenerating agents of the present invention were tested on a mouse model of nephropathy induced by ischemia-reperfusion via ligation of the left renal artery. As a result, the G-CSF group improved in tubular damage and thyroidization over the control group. The G-CSF group also showed significant improvement in BUN (blood urea nitrogen) level over the control group. Thus, it was confirmed that G-CSF is useful as a therapeutic agent for renal diseases. Moreover, these results show that the renal tissue necrosed by artery ligation was repaired/regenerated by administering G-CSF, thus suggesting that G-CSF is useful as a renal repairing/regenerating agent.

The following examples further illustrate the present invention without, however, limiting the scope of the invention thereto. Various changes and modifications can be made by those skilled in the art on the basis of the description herein, and such changes and modifications are also included in the present invention.

Example

Example 1

Left renal artery of B6 mouse was ligated for 60 minutes followed by release of the ligation to allow reperfusion, and from the following day, 100 µg/kg of G-CSF was subcutaneously (s.c.) administered twice a day in the morning and evening for 5 days. One month after the treatment, the animals were necropsied and both kidneys were fixed with formalin and then pathological findings were evaluated. As a control, vehicle, which is diluent for G-CSF, was administered in control group mice.

This model is considered to be a nephropathy model because of strong evidence of tubular damage and thyroidization in the kidney. The renal injury of this model mainly includes tubular atrophy or partial necrosis, showing ischemic renal injury resembling clinical atherosclerotic nephropathy or diabetes-induced atherosclerotic nephropathy.

In the present example, renal pathological findings were evaluated for tubular damage and thyroidization on the basis of the following criteria.

(1) Tubular damage
−: No change.
±: Mild damage to distal tubules.
+: Damage mainly to distal tubules.

++: Damage of proximal tubules in addition to distal tubules.
+++: Tubular atrophy as a whole.
(2) Thyroidization (thyroid-like formation due to urinary protein accumulation)
−: No change.
±: Slightly found.
+: Found in about ¼.
++: Found in about ⅓.
+++: Found in ½ or more.
The pathological findings are shown below.

TABLE 1

Table: Influence of G-CSF on the renal lesion after ischemia-reperfusion

| Group | Number of animals | Tubular atrophy (%) | | | | | Thyroidization (%) | | | | |
|---|---|---|---|---|---|---|---|---|---|---|---|
| | | − | ± | + | ++ | +++ | − | ± | + | ++ | +++ |
| Vehicle | 11 | 0 | 9 | 18 | 72 | 0 | 0 | 9 | 18 | 63 | 9 |
| G-CSF | 10 | 0 | 0 | 60 | 40 | 0 | 0 | 10 | 80 | 10 | 0 |

The highest percentage of tubular atrophy in the vehicle group was 72% at stage ++ in contrast to the G-CSF group in which the percentage at stage ++ decreased to 40%.

The highest percentage of thyroidization in the vehicle group was 63% at stage ++ in contrast to the G-CSF group in which the percentage at stage ++ decreased to 10%.

The BUN (blood urea nitrogen) level in the peripheral blood was determined to examine the influence on renal function. As a result, the BUN of the G-CSF group (24.7+/−0.7 mg/dL) was improved significantly than that in the control group (32.1+/−1.4 mg/dL) ($p<0.001$).

These results show that G-CSF is useful as a therapeutic agent for renal diseases.

Moreover, these results show that the renal tissue necrosed by artery ligation was repaired/regenerated by G-CSF administration, thus suggesting that G-CSF is useful as a renal repairing/regenerating agent.

The invention claimed is:

1. A method for proliferating or regenerating renal tissue or a cell present in renal tissue by
    contacting granulocyte colony-stimulating factor (G-CSF) in an effective amount proliferation or regeneration, with the renal tissue or the cell present in renal tissue,
    wherein the renal tissue is in a state of diabetic nephropathy and wherein said tissue or cell thereby proliferates or regenerates.

2. A method for treating a renal disease in a patient with diabetic nephropathy in need of said treatment, comprising
    administering to said patient G-CSF as an active ingredient in an amount effective or sufficient for the treatment of diabetic nephropathy.

3. A method for repairing/regenerating renal tissue in a state of diabetic nephropathy,
    comprising administering an effective amount therefor of G-CSF as an active ingredient, wherein said tissue is repaired/regenerated.

4. The method of claim 1, wherein the renal tissue is an injured kidney, a necrotic kidney or a resected kidney.

5. The method of claim 4, wherein the kidney is a kidney injured by a drug or necrosed by insufficient blood flow.

* * * * *